US00PP17819P3

(12) United States Plant Patent
Jennings

(10) Patent No.: US PP17,819 P3
(45) Date of Patent: Jun. 19, 2007

(54) RASPBERRY PLANT NAMED 'MARCELA'

(50) Latin Name: *Rubus idaeus*
Varietal Denomination: Marcela

(75) Inventor: Derek L. Jennings, Maidstone (GB)

(73) Assignee: Medway Fruits, Otham, Maidstone, Kent (GB)

( * ) Notice: Subject to any disclaimer, the term of this patent is extended or adjusted under 35 U.S.C. 154(b) by 61 days.

(21) Appl. No.: 11/181,725

(22) Filed: Jul. 15, 2005

(65) Prior Publication Data

US 2007/0016986 P1 Jan. 18, 2007

(51) Int. Cl.
*A01H 5/00* (2006.01)

(52) U.S. Cl. ..... Plt./204

(58) Field of Classification Search ..... Plt./204
See application file for complete search history.

*Primary Examiner*—Kent Bell
*Assistant Examiner*—June Hwu
(74) *Attorney, Agent, or Firm*—Buchanan Ingersoll & Rooney PC

(57) ABSTRACT

A new and distinct *Rubus idaeus* L. plant is provided that is the product of a controlled breeding program. The new Raspberry plant abundantly forms attractive conical-shaped Claret Rose fruit which is lighter in coloration than that of the 'Autumn Bliss' cultivar (U.S. Plant Pat. No. 6,597) when mature. The new cultivar displays spiney stems and canes unlike the 'Joan Squire' cultivar (non-patented in the United States). The fruit is very firm and is firmer than that of the 'Autumn Bliss' cultivar, and is well suited for consumption as high grade fresh fruit. The very firm nature of the mature fruit is advantageous during harvest, shipment, and marketing.

1 Drawing Sheet

Figure 1:
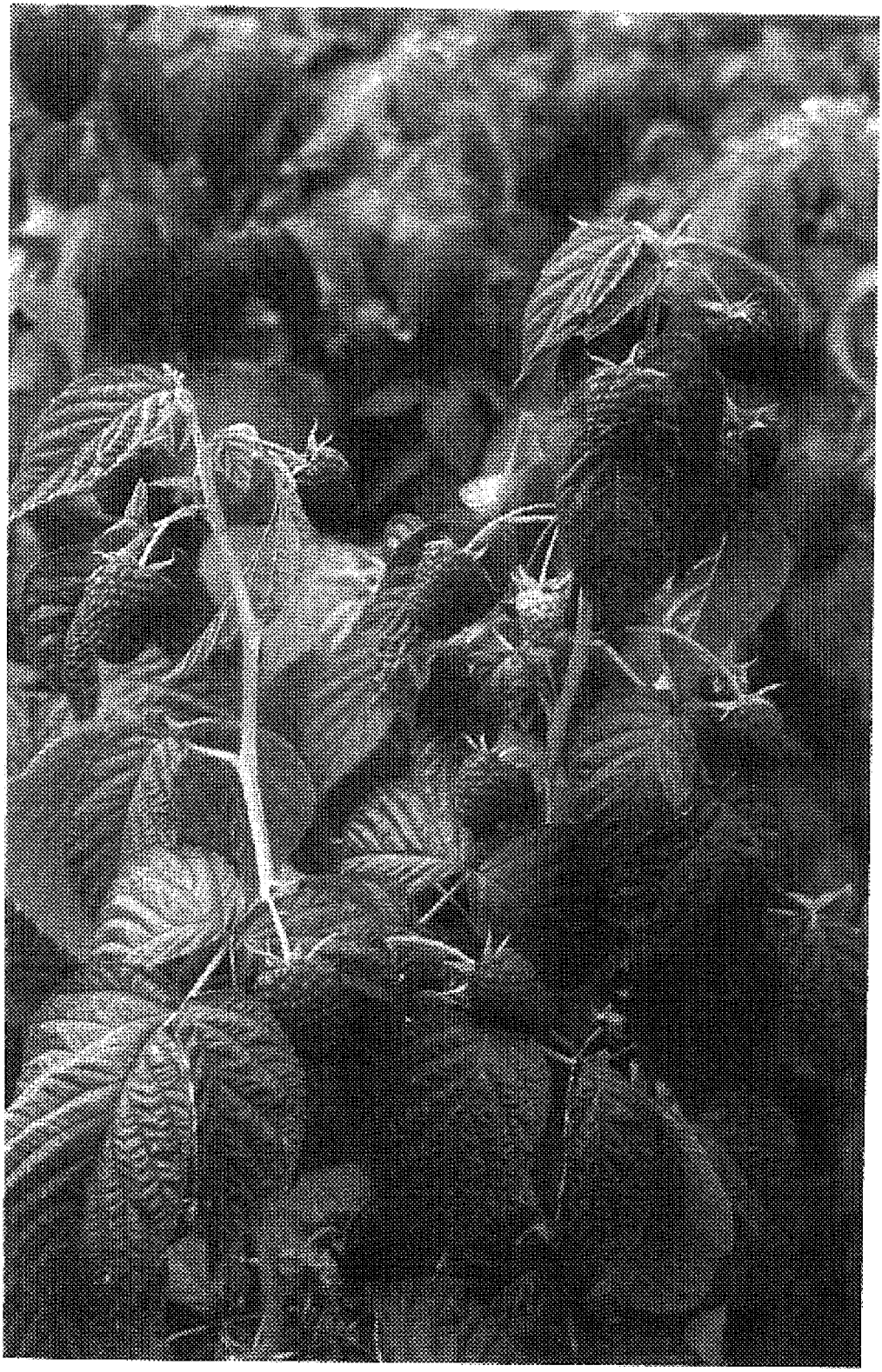

Botanical/commercial classification: *Rubus idaeus*/Raspberry Plant.
Varietal denomination: cv. Marcela.

SUMMARY OF THE INVENTION

The instant plant (i.e., *Rubus idaeus* L.) was created in the course of a planned breeding program carried out at Maidstone, Kent, United Kingdom. Two parents were crossed in the hope that they would contribute the desired characteristics. The female parent (i.e., the seed parent) was the 'Autumn Bliss' cultivar (U.S. Plant Pat. No. 6,597). The male parent (i.e., the pollen parent) was the 'Joan Squire' cultivar (non-patented in the United States and the subject of European Plant Breeders Rights Grant No. 5680). The 'Joan Squire' cultivar is a cross between two hybrids of complex origin. The parentage of the new cultivar can be summarized as follows:

'Autumn Bliss'×'Joan Squire'.

The seeds resulting from the above pollination were sown and small plants were obtained which were physically and biologically different from each other. Selective study resulted in the identification of a single plant of the new cultivar.

It was found that the new Raspberry plant of the present invention possesses the following combination of characteristics:

(a) abundantly forms attractive glossy conical-shaped Claret Rose fruit which is lighter in coloration than that of the 'Autumn Bliss' cultivar when mature, (b) displays spiny stems and canes unlike the 'Joan Squire' cultivar, and (c) produces very firm fruit that is firmer than that of the 'Autumn Bliss' cultivar and is well suited for consumption as high grade fresh fruit.

The new cultivar well meets the needs of the berry industry. The very firm nature of the mature fruit is advantageous during picking, shipment and marketing.

The new cultivar can be readily distinguished from its 'Autumn Bliss' parent in view of its lighter colored mature fruit and its greater fruit firmness. Also, the new cultivar can be distinguished from its 'Joan Squire' parent by the presence of spines on the stems and canes which are absent on this parent cultivar.

The new cultivar has been found to undergo asexual propagation at Maidstone, Kent, United Kingdom by in vitro tissue culture and by the rooting of cuttings. Asexual propagation by the above-mentioned methods as performed at such location has shown that the characteristics of the new cultivar are strictly transmissible from one generation to another. Accordingly, the new variety undergoes asexual propagation in a true to type manner.

The new cultivar initially was designated MF941/3, and subsequently has been named 'Marcela'.

BRIEF DESCRIPTION OF THE PHOTOGRAPH

The accompanying photograph shows as nearly true as is reasonably possible to make the same in a color illustration of this character a typical specimen of the new cultivar. The photograph was obtained on Jul. 31, 2003 at Maidstone, Kent, United Kingdom. The illustrated plant had been planted during the Spring of 2002.

FIG. 1 illustrates a fruiting plant where the foliage and fruit in various stages of development are illustrated. The attractive Claret Red conical-shaped mature fruit of the new cultivar is shown.

DETAILED DESCRIPTION

The chart used in the identification of color is that of The Royal Horticultural Society (R.H.S. Colour Chart). The description is based on the observation of specimens of the new cultivar growing at Maidstone, Kent, United Kingdom.

Botanical Classification: *Rubus idaeus* L.

Plant: The new variety is being grown for its primocane fruit crop. Displays a generally upright growth habit with a medium number of current season's canes. On a very young rapidly growing shoot anthocyanin coloration is absent at the apex. On a current season's cane anthocyanin coloration is either absent or very weak, the internode length is short, a medium quantity of bloom is present, and the length of the vegetative buds is medium. Primocanes commonly reach a length of approximately 1.8 meters and are Red Group 53A in coloration. A waxy coat is absent on the primocanes. The time of cane emergence is generally comparable to that of the 'Autumn Bliss' cultivar. Short greenish-brown spines having a small base are sparsely present on the stems and canes. Commonly approximately 1 thorn having a length of approximately 1 to 2 mm is present over a length of 25 mm of an actively growing primocane.

Foliage: The predominant number of leaflets commonly is approximately equally divided among three and five. Terminal leaflets commonly are approximately 13 cm in length and approximately 10 cm in width. The leaflets are Green Group 137C on the upper surface, Green Group 138B on the under surface, generally concave in cross section, semi-glossy on the upper surface, possess numerous shallow serrations, possess a strongly cuspidate apex, possess a cordate base, and possess weak rugosity. The lateral leaflets are freely positioned. Spines are either absent or very few in number on the leaf pedicels. The petioles commonly are spiny, Green Group 138D in coloration, and commonly measure approximately 8 cm in length for mature leaves. The stipules commonly possess tapered points, measure approximately 1 cm in length, and are Green Group 138D in coloration.

Flowering: Begins very early on current season's canes and generally is comparable to the 'Ariadne' cultivar (non-patented in the United States) in Southern England. The flower size is medium, and anthocyanin in coloration commonly is absent on the peduncle. The flowers are pure white, near White Group 155B, and the flower diameter commonly is approximately 2.3 cm inclusive of the sepals. The calyx consists of 5 sepals which commonly are Green Group 138B in coloration and approximately 1.5 cm in length. The peduncle for terminal fruits commonly is approximately 6.5 cm in length and bears spines.

Bearing type: Fruit is mainly borne on the current season's canes. The time of fruit ripening on a current season's cane is very early and generally is comparable to that of the 'Ariadne' cultivar, and the length of the fruiting period is medium.

Fruit: Generally conical-shaped in a lateral view and similar in shape to that of the 'Annamaria' and 'Rafzmach' cultivars (non-patented in the United States). The coloration of the mature fruit is Claret Rose, Red Group 50B, and commonly is lighter than that of its 'Autumn Bliss' ancestor. The coloration is similar to that of the 'Glen Clova' and 'Malling Orion' cultivars (non-patented in the United States). The internal fruit coloration commonly is near Red Group 52B. The mature fruit is very firm and is firmer than that of its 'Autumn Bliss' ancestor. Such firmness is beneficial during picking, handling, and when transporting to the marketplace. The fruit commonly is borne in small drupes. A strong glossiness is present on the surface of the fruit, and the adherence of the fruit to the plug is medium. The fruit size commonly becomes lesser as the season progresses. Initially the typical fruit weight is approximately 4.5 grams, the fruit length commonly is approximately 30 mm, and the fruit width commonly is approximately 22 mm. Towards the end of the fruiting season, the typical fruit weight is approximately 3 grams, the fruit length commonly is approximately 22 mm and the fruit width commonly is approximately 20 mm. A druplet number of approximately 60 commonly is initially displayed which commonly decreases to approximately 40 as the season progresses. Since the new cultivar is being grown for its primocane fruit crop, the fruiting propensity on floricanes has not been evaluated. However, the size of the fruit produced on floricanes is believed to be smaller than that produced on primocanes. A typical seed of the cultivar commonly measures approximately 3.2 mm in length, and approximately 350 of the seeds commonly weigh 1 gram. Typical fruit productivity at Maidstone, Kent, United Kingdom, has been observed to be 5t/ha.

Resistance to pests and diseases: During observations to date the new cultivar of the present invention has displayed adequate resistance to all pests and diseases encountered at Maidstone, Kent, United Kingdom.

Virus status: The virus status of the new cultivar has not been evaluated to date.

Market: The berries are suitable for consumption as a high grade fresh fruit and also are amenable to processing.

I claim:

1. A new and distinct cultivar of Raspberry plant having the following combination of characteristics:

(a) abundantly forms attractive glossy conical-shaped Claret Rose fruit which is lighter in coloration than that of the 'Autumn Bliss' cultivar when mature, (b) displays spiny stems and canes unlike the 'Joan Squire' cultivar, and (c) produces very firm fruit that is firmer than that of the 'Autumn Bliss' cultivar and is well suited for consumption as high grade fresh fruit;

substantially as illustrated and described.

* * * * *